United States Patent [19]

Renner et al.

[11] 4,082,768
[45] Apr. 4, 1978

[54] NEW IMIDES OF UNSATURATED DICARBOXYLIC ACIDS, PROCESSES FOR THEIR MANUFACTURE, AND THEIR USE

[75] Inventors: Alfred Renner, Munchenstein; Theobald Haug, Frenkendorf, both of Switzerland

[73] Assignee: Ciba-Geigy Corporation, Ardsley, N.Y.

[21] Appl. No.: 687,791

[22] Filed: May 19, 1976

Related U.S. Application Data

[62] Division of Ser. No. 381,328, Jul. 20, 1973, Pat. No. 3,960,812.

[51] Int. Cl.² ............... C07D 403/112; C07D 403/14
[52] U.S. Cl. ............... 260/326.26; 260/47 UA; 260/47 CP; 260/49; 260/78 A; 542/415; 542/416; 542/402
[58] Field of Search ............... 260/326.26

[56] References Cited

U.S. PATENT DOCUMENTS

| | | | |
|---|---|---|---|
| 3,651,012 | 3/1972 | Holub et al. | 260/326.26 |
| 3,732,189 | 5/1973 | Crevello et al. | 260/326.26 |
| 3,742,089 | 6/1973 | Schroeter | 260/326.26 |
| 3,756,951 | 9/1973 | Dickert | 260/326.26 |
| 3,766,302 | 10/1973 | Holub et al. | 260/326.26 |

*Primary Examiner*—R. Gallagher
*Assistant Examiner*—Mary C. Vaughn
*Attorney, Agent, or Firm*—Luther A. R. Hall

[57] ABSTRACT

New bis-imides and tris-imides of the formula

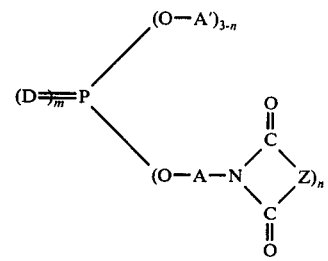

in which A and A' denote aromatic radicals which are optionally substituted or interrupted by an oxygen atom, an alkylene group or a sulphonyl group, Z denotes a radical of the formulae

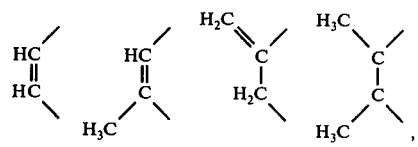

D denotes an oxygen atom or sulphur atom, m denotes the number 1 or 0 and n denotes the number 2 or 3, are obtained by cyclizing dicarboxylic acid monoamide compounds of the formula

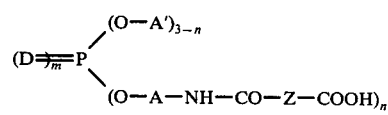

with elimination of water.

The bis-imides and tris-imides, mixed with azomethines and optionally with curing catalysts, can be used for the manufacture of moulded materials having technically very valuable mechanical and dielectric properties.

3 Claims, No Drawings

NEW IMIDES OF UNSATURATED DICARBOXYLIC ACIDS, PROCESSES FOR THEIR MANUFACTURE, AND THEIR USE

This is a divisional of application Ser. No. 381,328 filed on July 20, 1973, now U.S. Pat. No. 3,960,812.

The present invention relates to new N,N'-bis-imides and N,N',N''-tris-imides, containing a phosphate, thiophosphate or phosphite group, of certain unsaturated dicarboxylic acids, a process for their manufacture and the use of the new bis-imides and tris-imides in thermosetting mixtures, containing azomethines, for the manufacture of moulded materials.

The subject of the present invention are new bis-imides and tris-imides of the general formula I

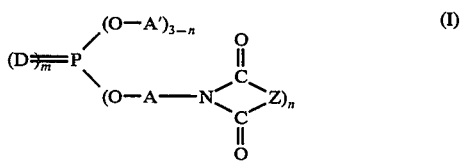

in which A and A' denote aromatic radicals which are optionally substituted or interrupted by an oxygen atom, an alkylene group or a sulphonyl group, Z denotes a radical of the formulae

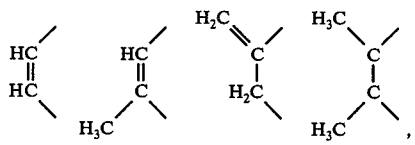

D denotes an oxygen or sulphur atom, $m$ denotes the number 1 or 0 and $n$ denotes the number 2 or 3.

Preferably, in the formula I, A and A' denote identical or different aromatic radicals with 6 to 12 carbon atoms, Z denotes the vinylene radical, D denotes an oxygen atom or sulphur atom, $m$ is 1 and $n$ is 3.

The aromatic radicals A and A' can be substituted by groups or atoms which do not interfere with the course of the reaction when manufacturing the new imides. As such groups or atoms there may be mentioned, for example, linear or branched alkyl radicals with 1–4 carbon atoms, halogen atoms, the nitro group, the tertiary amino group, the alkoxy group, the carbalkoxy group or the carbamide group.

The new bis-imides and tris-imides of the formula I are obtained by cyclising dicarboxylic acid monoamide compounds of the general formula II

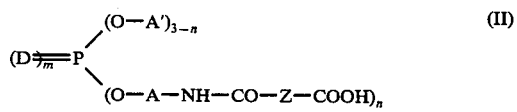

at temperatures below 90° C in the presence of catalysts, with elimination of $n$ mols of water, and subsequently isolating the compounds of the formula I by precipitating the reaction product in water or an aqueous alcohol solution.

U.S. Pat. No. 2,444,536 provides general instructions for the manufacture of simple N-arylmaleimides, according to which fused, anhydrous sodium acetate serves as the catalyst in the dehydrating cyclisation of the appropriate maleamic acid to the maleimide. The use of specially anhydrous sodium acetate appears thus to be sensible; the absence of water, that is to say even of water of crystallisation, should have a favourable influence on the cyclisation.

Against this, it has been found that the dehydrating cyclisation of the dicarboxylic acid monoamides of the formula II to give the corresponding bis-imides or tris-imides of the formula I also takes place in the presence of hydrated alkali metal salts of the lower monocarboxylic acids without the yield being reduced thereby. If the salts are used unfused, the reaction products are even frequently less dark in colour.

The solvents used in the dehydrating cyclisation reaction are the anhydrides of the lower aliphatic monocarboxylic acids. As examples of anhydrides there may be mentioned acetic anhydride, propionic anhydride, butyric anhydride and isobutyric anhydride.

The use of acetic anhydride in a 1.2-fold amount, relative to the amount by weight of the dicarboxylic acid monoamide of the formula II, is preferred.

The sodium salts or potassium salts of the same monocarboxylic acids can be used as catalysts in the dehydrating cyclisation.

The use of sodium acetate in an amount of 5 – 15 percent by weight relative to the amount of the amide-acid of the formula II, is preferred.

According to the abovementioned U.S. patent specification, the N-arylmaleimides are isolated from the reaction mixture by stirring the latter into a large amount of water. This method is unsuitable for isolating the imides of the formula I according to the invention, since resinous by-products also precipitate and can only be removed with difficulties. On the other hand, a lower aliphatic alcohol with up to 6 carbon atoms in the molecule or a cycloaliphatic alcohol, optionally mixed with a little water, proved substantially better as the precipitant. In this case, a crystalline product of sufficient purity is obtained immediately.

As examples of such alcohols there may be mentioned: Methanol, ethanol, propanol, isopropanol, butanol, isobutylalcohol, hexanol and cyclohexanol; isopropanol is preferred. The mixing ratio between the alcohol or the sum of the alcohols and the water can vary between 6:1 and 1:6. An anhydrous alcohol or a mixture of these anhydrous alcohols can also serve to precipitate the new imides of the formula I from the reaction mixture. Equally, it is possible to add the precipitant direct to the reaction batch. The temperature during the precipitation can be 0°–50° C. The precipitation of the new imides of the formula I from the reaction mixture is advantageously effected by adding a mixture of 1 part of water and 2–4 parts of isopropanol at 5°–25° C. The amount of the precipitant is normally 1.5 to 3 times the amount by weight of the reaction batch.

The dicarboxylic acid monoamide compounds of the formula II are obtained according to known processes, by causing $n$ mols of maleic anhydride, citraconic anhydride, itaconic anhydride or dimethylmalic anhydride to undergo an addition reaction with 1 mol of bis- or tris-(aminoaryl)-phosphate, -thiophosphate or -phosphite of the general formula III

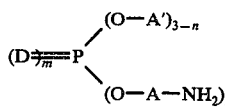   (III)

The aminoaryl compounds of the formula III are obtained analogously to the process described in British Patent Specification No. 1,027,059 by trans-esterification of, for example, triphenylphosphate, triphenylthiophosphate or triphenylphosphite with aminophenols of the general formula IV $$HO - A - NH_2 \quad\quad (IV)$$

optionally mixed with phenols of the formula V $$A' - OH \quad\quad (V)$$

the molar ratio of aminophenols of the formula IV to phenols of the formula V being 2:1 if a phenol mixture is used.

The aminoaryl compounds of the formula III can also be obtained according to the process described in German Auslegeschrift (DAS) No. 1,257,153, by reaction of phosphorus trihalide, phosphoryl trihalide or triophosphoryl trihalide with the aminophenols of the formula IV optionally mixed with the phenols of the formula V, the molar ratio being as indicated above if a phenol mixture is used.

As suitable aminophenols of the formula IV there may be mentioned: m-Aminophenol, p-aminophenol and aminophenols substituted by alkyl groups or chlorine atoms, such as 2-methyl-4-aminophenol and 2-chloro-4-aminophenol. It is furthermore possible to use polynuclear aminophenols, such as 1,2-amino-naphthol, 1,5-aminonaphthol, 1,6-aminonaphthol, 1,7-aminonaphthol, 2,7-aminonaphthol, p-hydroxyphenyl-p-aminophenyl-dimethylmethane and p-hydroxyphenyl-p-amino-phenylsulphone.

As phenols of the formula V there should in particular be mentioned: Phenol, phenol substituted by alkyl groups or halogen atoms, naphthol or naphthol substituted by alkyl groups or halogen atoms.

As bis-imides or tris-imides of the formula I there may be mentioned: The bis-maleimide of 4,4-diamino-triphenyl-phosphate, the bis-citraconimide of 4-tert.-butyl-4',4"-diaminotriphenylphosphate, the bis-maleimide of 3,3'-diamino-3"-dimethylaminotriphenylphosphate, the bis-itaconimide of bis-(4-aminophenyl)-bis-phenylylphosphate, the bis-maleimide of bis-(4-aminophenyl)-2-naphthylphosphate, the tris-maleimide of tris-(4-aminophenyl)-phosphate, the tris-citraconimide of tris-(4-aminophenyl)-phosphate, the bis-maleimide of 4,4'-diamino-triphenyl-phosphite, the N,N'-bis-maleimide of diamino-triphenyl-thiophosphate, the N,N',N"-tris-maleimide of tris-(4-aminophenyl)-phosphite, and the N,N',N"-tris-maleimide of tris-(4-aminophenyl)-thiophosphate.

The new bis-imides and tris-imides of the formula I are interesting compounds for plastics chemistry, since, when mixed with azomethines, they can be heat-cured to give moulded materials having technically valuable properties.

"Tetrahedron" 27, page 2,203 et seq., describes the addition of 2 molecules of a N-substituted maleimide to an azomethine. However, this reaction is rather unfavourable, as is shown by the low yields, averaging only 40%. Furthermore, the addition reaction described has the disadvantage that it takes place comparatively very slowly. According to the abovementioned publication, for example, a mixture consisting of N-phenylmaleimide and N,N-dimethylbenzylidenemethylamine only gives 32% of the adduct theoretically to be expected, after continuous heating for 600 minutes at 135° C.

It has now been found that mixtures of the imides according to the invention, of the formula I, and azomethines can be reacted practically quantitatively on heating, the reaction taking place very rapidly. By way of comparison, heating a mixture according to the invention consisting of tris-maleimide and an azomethine to 135° C gives a reaction product which is already cured after 43 minutes. The mixtures according to the invention, which are stable on storage at room temperature furthermore have the advantage that after curing they give modulated materials having technically valuable properties.

As compared to the moulded materials manufactured from bis-maleimides and diamines, as described in French Pat. No. 1,555,564, the moulded materials obtained from the curable mixtures according to the present invention show the advantage of greater resistance to heat distortion.

It was to be expected that the new thermosetting mixtures according to the present invention, because of their phosphous content, would be less inflammable than the moulded materials according to the French patent specificiation or than moulded materials which are manufactured from the known bis-maleimides, for example N,N'-4,4'-diaminodiphenylmethanel-bis-maleimide, and azomethines. Because of the 50% greater density of crosslinking of the mouldings based on a N,N',N"-tris-maleimide according to the invention and an azomethine, poorer mechanical properties of the new products would have been expected; for example, the mouldings should have been more brittle. Surprisingly, however, mouldings according to the invention, including those based on N,N',N"-tris-imides, are more flexible, and have a distinctly higher flexural strength and impact strength, for the same heat distortion point, than mouldings which have been manufactured from a bis-maleimide and an azomethine. This situation is shown in Table I.

Hence a further subject of the present invention are new, storage-stable, thermosetting mixtures which are characterised in that they contain (a) N,N'-bis-imides and/or N,N',N"-tris-imides of the general formula I, (b) azomethines of the general formulae

 (VI),

 (VII)

or

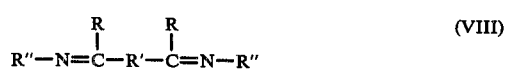 (VIII)

in which R denotes a hydrogen atom, a linear or branched aliphatic hydrocarbon radical with up to 12 carbon atoms, a cycloaliphatic or cycloaliphatic-aliphatic hydrocarbon radical with up to 12 carbon atoms, an aromatic radical with 6 – 12 carbon atoms, an araliphatic hydrocarbon radical with up to 20 carbon atoms or a heterocyclic or heterocyclic-aliphatic radical, R' and R", with the exception of the meaning of a hydrogen atom, have the same meaning as R, and R' together with R and with the inclusion of the C atom carrying the two substituents can also denote a cycloaliphatic ring system, and E denotes a divalent organic radical with at least 2 and at most 30 carbon atoms, and optionally (c) a curing catalyst.

Preferably, the mixtures according to the invention consist of (a) tris-imides of the formula I, in which A and A' denote identical or different aromatic radicals with 6 to 12 carbon atoms, Z denotes the vinylene radical, D denotes an oxygen or sulphur atom, $m$ is 1 and $n$ is 3, and (b) azomethines of the formulae VI and VII, in which R denotes a hydrogen atom, R' and R" each denote a phenyl radical and E denotes a radical of the formulae

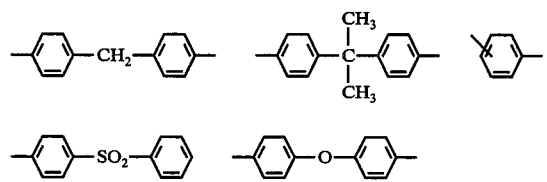

The symbol E in the formula VII can denote a linear or branched alkylene radical with fewer than 20 carbon atoms, a phenylene radical, a cyclohexylene radical or a radical of the formula

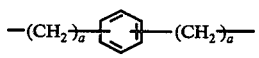

in which $a$ represents an integer from 1 to 3.

The symbol E can also embrace several phenylene or cyclohexylene radicals which are linked directly or via a single valency bond or via an atom or a divalent inert group such as, for example, oxygen of sulphur atoms or alkylene groups with 1 to 3 carbon atoms, or via the following groups: —CO—, —SO$_2$—, —NR—, —N=N—, —CONH—, —COO— and —CONH—E—H-NCO—.

Furthermore, the various phenylene or cyclohexylene radicals can be substituted by methyl groups.

The symbol E can also represent the grouping

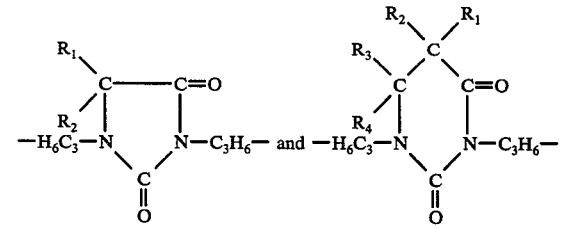

Herein, R$_1$, R$_2$, R$_3$ and R$_4$ denote hydrogen atoms or identical or different aliphatic hydrocarbon radicals with 1 – 6 carbon atoms, and R$_1$ and R$_2$ together with the caron atom in position 5 can also form a 5-membered or 6-membered aliphatic ring.

As special examples of the imides of the formula I there should in particular be mentioned: The bis-maleimide of 4,4'-diamino-triphenylphosphate and the tris-maleimide of tris-(4-aminophenyl)phosphate. Advantageously, mixtures of different imides can also be used.

The azomethines of the formulae VI and VII are a known class of compound and are obtained by reacting aldehydes or ketones of the formula IX

wherein R and R' have the same meaning as in the formulae VI and VII, with monoamines of the formula X $$R" — NH_2 \qquad (X)$$

or diamines of the formula XI

wherein R" and E have the same meaning as in the formula VIII or VII, in equivalent amounts and optionally in the presence of a catalyst.

The azomethines of the formula VIII are also known compounds and are manufactured analogously by reacting dialdehydes or diketones of the formula XII

wherein R and R' have the same meaning as in the formula VIII, with monoamines of the formula X in equivalent amounts and optionally in the presence of a catalyst.

The azomethines of the formulae VI, VII and VIII can be manufactured according to one of the known processes, of which, for example, a summarising description is given in "Houben-Weyl", Methoden der organischen Chemie (Methods of Organic Chemistry), volume 11/2 (1958), page 73 et seq.

In the azomethines of the formulae VI, VII and VIII, the radicals R, R' and R", if they denote an aliphatic or araliphatic radical, can also contain the groupings —O—, —SO$_2$—, —CONH— or —COO— in the hydrocarbon chain. Where the radicals R, R' and R" represent aliphatic, aromatic, araliphatic, cycloaliphatic, cycloaliphatic-aliphatic or heterocyclic radicals, these radicals can also be substituted by groups which on curing the mixture do not have an adverse influence on the addition mechanism. As examples of such groups there may be mentioned: Halogen atoms, alkyls, alkoxyls, —NO$_2$, —CONH, COOX (X = alkyl) and SO$_2$. The heterocyclic and heterocyclic-aliphatic radical can contain the following hetero-atoms or hetero-groups: —O—, —SO$_2$—, —S—, —SO— and =N— or —NH—; preferably, the heterocyclic radical denotes a N,N-heterocyclic radical.

As carbonyl compounds of the formulae IX and XII for the manufacture of the azomethines of the formulae VI, VII or VIII there may in particular be mentioned: Acetaldehyde, propionaldehyde, isobutyraldehyde, butyraldehyde, caproaldehyde, caprylaldehyde, capraldehyde, tetrahydrobenzaldehyde, hexahydrobenzaldehyde, furfuraldehyde, benzaldehyde, 2-methylbenzaldehyde, p-methoxy-benzaldehyde, β-naphthaldehyde, acetone, methyl ethyl ketone, dibutyl ketone, diheptyl ketone, didecyl ketone, dibenzyl ketone, acetophenone, butyrophenone, benzophenone, 2-methylacetophenone, 4-methoxypropiophenone, cyclopentanone, cyclohexanone, terephthalaldehyde, isophthalaldehyde, glyoxal, glutaraldehyde and acetonylacetone.

As monoamines of the formula X for the manufacture of the azomethines of the formulae VI or VII there may in particular be mentioned: Methylamine, butylamine, iso-butylamine, hexylamine, dodecylamine, cyclohexylamine, benzylamine, aniline, toluidine, α-naphthylamine and β-naphthylamine.

As diamines of the formula XI for the manufacture of the azomethines of the formula VII there may in particular be mentioned: Ethylenediamine, 1,6-hexamethylenediamine, 3,3,5-trimethyl-1,6-diaminohexane, isophoronediamine, m-phenylenediamine, p-phenylenediamine, 4,4'-diamino-diphenyl-methane, 3,3'-dichloro-4,4'-diamino-diphenyl-methane, 4,4'-diamino-diphenyl-ether, 4,4'-diamino-diphenyl-sulphone, 4,4'-diamino-dicyclohexyl-methane, m-xylylenediamine, p-xylylenediamine, 4,4'-diamino-1,1'-diphenyl-propane and bis-(γ-amino-propyl)-5,5-dimethylhydantoin.

As special azomethines there may be mentioned: N,N'-bis-(benzylidene)-hexamethylenediamine, N,N'-bis-(benzylidene)-p-phenylenediamine, N,N'-bis-(benzylidene)-diaminodiphenyl-methane, benzylidenebutyl-amine and benzalaniline.

In the publication "Tetrahedron" 27, page 2,203 et seq., already cited, the molar ratio of N-substituted maleimide to azomethine is so chosen that 2 maleimide groups are present in the reaction mixture per C=N— group. It has been shown that an excess of imide groups over the ratio disclosed in the cited publication can result in advantages. Since a tris-imide of the formula I by itself cures thermally more slowly than a mixture according to the cited publication, it would have been expected that an excess of imide groups over the ratio indicated in the cited publication would lead to slower curing. Surprisingly, however, a mixture in which more than 2 imide groups are present per >C=N— group even cures somewhat more rapidly than a mixture in which only 2 imide groups are present per >C=N— group. This situation is demonstrated in Table II, which shows the curing times of various mixtures of tris-maleimide with azomethines and of tris-maleimide by itself at 135° C and 160° C.

In the curable mixtures according to the present invention the molar ratio of imides of the formula I to the azomethines of the formula VI can be varied from 1:1.5 to 3:1.5 whilst the molar ratio of imides of the formula I to the azomethines of the formula VII or VIII can be between 1.3:1 and 4:1.

The mixtures which are stable to storage at room temperature can also consist of several imides of the formula I and several azomethines of the formulae VI, VII and VIII.

The curing of the mixtures according to the invention is effected by warming the mixtures to temperatures between 100° and 280° C, preferably 150° and 220° C, whereupon the mixtures are converted into crosslinked, insoluble and infusible products, without giving off volatile reaction products.

It is also possible first to manufacture a prepolymer from the mixtures according to the invention by heating the homogeneously mixed, optionally finely ground starting materials for a time to 50° - 140° C, so that a partially soluble product which is still thermoplastic is produced. This prepolymer must under certain circumstances be ground to give a processable powder. The prepolymerisation can also be effected by heating a solution or suspension of the starting materials. For this, substances which do not react with the starting materials and which, if desired, adequately dissolve then, can be used. Examples of such liquids are: Dimethylformamide, tetramethylurea, dimethylsulphoxide, N-methylpyrrolidone, dichloroethylene, tetrachloroethylene, tetrachloroethane, tetrabromoethane, chlorobenzene, dichlorobenzene, bromobenzene, cyclohexanone, dioxane or alkylated aromatic hydrocarbons.

For some technical applications, the addition of a curing catalyst is advantageous. For example, the cured state is reached more rapidly by adding a small amount of an organic peroxide or per-salt. For this purpose compounds such as di-tert.-butyl peroxide, dilauryl peroxide, dicumyl peroxide, tert.-butyl cumyl peroxide or tert.-butyl perbenzoate, used in a concentration of 0.01 - 5 percent, preferably 0.25 - 0.5 percent, relative to the total weight of the curable mixture, are suitable. It is however also possible to use other, non-peroxidic, curing accelerators or additives which have a favourable influence on the curing reaction.

The curable mixtures according to the invention are employed above all in the fields of surface protection, the electrical industry, laminating processes and the building industry. They can be used in a formulation suited in each case to the particular application, in the unfilled or filled state, if appropriate in the form of solutions or dispersions, as lacquers, compression moulding compositions, sintering powders, dipping resins, casting resins, injection moulding formulations, impregnating resins, binders and laminating resins.

Hence, a further subject of the invention is a process for the manufacture of crosslinked, insoluble and infusible plastics products, characterised in that the imides of the formula I and azomethines of the formulae VI, VII or VIII, optionally in the presence of a curing catalyst, are reacted with one another at temperatures between 100° and 280° C.

The manufacture, according to the invention, of the crosslinked infusible products is as a rule carried out with simultaneous shaping to give mouldings, sheet-like structures, laminates or adhesive bonds. For these purposes, additives which are customary in the technology of curable plastics, such as fillers, plasticisers, pigments, dyestuffs, mould release agents and flameproofing substances, can be added to the curable mixtures. Glass fibres, mica, quartz powder, kaolin, colloidal silicon dioxide or metal powders are examples of fillers which can be used whilst calcium stearate is an example of a mould release agent which can be used. Moulding can be effected by brief rapid heating, preferably to 150° - 220° C, under a pressure of 1 - 200 kp/cm². The mouldings thereby produced already have sufficient mechanical strength, so that they can be completely cured outside the press in an oven at 180° - 280° C.

If a prepolymer is first manufactured from the curable mixtures, the latter can be ground to a fine powder and then used as a surface protection agent, employing the fluidised bed process.

A solution or suspension of the prepolymer in a suitable solvent can be used for the manufacture of laminates by impregnating porous sheet-like structures such as fabrics, fibre mats or fibre fleeces, especially glass fibre mats or glass fibre fabrics, with solutions or suspensions and removing the solvent by a drying process. The further curing is carried out in a press, preferably at 170° – 250° C and 5 – 200 kp/cm² pressure. It is also possible merely to precure the laminates in the press and to post-cure the products thus obtained in an oven at 200°–280° C until optimum use properties are achieved. A very advantageous factor for the manufacture of laminates is that, for example, the solubility of the tris-maleimide of tris-(4-aminophenyl)-phosphate in dioxane is approximately twice as great as that of the previously frequently used N,N′-4,4′-diaminodiphenyl-methane-bis-maleimide.

EXAMPLE 1

(a) 294 g (3.0 mols) of maleic anhydride, dissolved in 800 ml of dioxane, are initially introduced into a reaction vessel provided with a stirrer and thermometer. A solution of 371 g (1 mol) of tris-(4-aminophenyl)-phosphate, dissolved in 2.5 liters of dioxane, is added dropwise to this solution over the course of 4 – 5 hours at 10° – 20° C. After completion of the addition, the mixture is stirred for a further 1½ hours and the reaction product is then filtered off, washed with chloroform and dried. 669 g of a yellowish substance of melting point 127° – 130° C are obtained. According to analytical data this has the following structure:

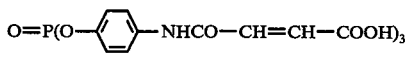

(b) 85 g of sodium acetate and 1.1 liters of acetic anhydride are initially introduced into a reaction vessel provided with a stirrer and thermometer and are warmed to 60° C by means of an oil bath. 954 g of the tris-maleamic acid manufactured according to (a) are added in portions to this solution over the course of 30 minutes in such a way that the reaction temperature does not exceed 90° C. After completion of the addition, the mixture is allowed to cool to room temperature and a mixture of 2 liters of isopropanol and 0.7 liter of water is subsequently added dropwise to the reaction products which have partially crystallised out. The substance which has precipitated is filtered off, washed with isopropanol and water until free of acid and dried. 532 g of a substance of melting point 173.5° – 177° C are obtained; according to analytical data, the substance is the tris-maleimide of tris-(4-aminophenyl)-phosphate, having the following structural formula:

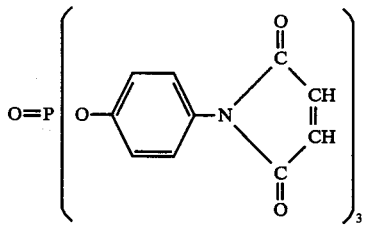

EXAMPLE 2

(a) 117.6 g (1.20 mols) of maleic anhydride dissolved in 500 ml of chloroform are initially introduced into a reaction vessel provided with a stirrer and thermometer. A solution of 154.8 g (0.40 mol) of tris-(4-aminophenyl)-thiophosphate in 600 ml of dioxane is added dropwise to this solution at room temperature over the course of 4 hours. After completion of the addition, the crystal suspension is stirred for a further 4 hours at room temperature and thereafter the solid reaction product is filtered off, washed with chloroform and dried. 279 g of a yellowish substance melting at 153°–156° C are thus obtained. According to analytical data, this has the structure:

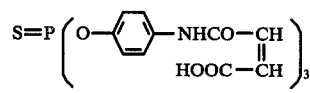

(b) 12 g of sodium acetate are suspended in 105 ml of acetic anhydride in a reaction vessel provided with a stirrer and thermometer and warmed to 90° C. 68 g of the tris-maleamic acid manufactured according to (a) are added in portions over the course of 15 minutes to the warm solution, the temperature being 85°–95° C. After completion of the addition, the mixture is stirred for a further 15 minutes at 85° C and thereafter a mixture of 50 ml of water and 250 ml of isopropanol is slowly added dropwise to the suspension. The suspension is left to stand overnight at room temperature and is subsequently filtered, and the residue is thoroughly washed with water and then dried. 56 g of a substance of melting point 232°–236° C are thus obtained; according to analytical data, this substance is the tris-maleimide of tris-(4-amino-phenyl)-thio-phosphate, having the following formula:

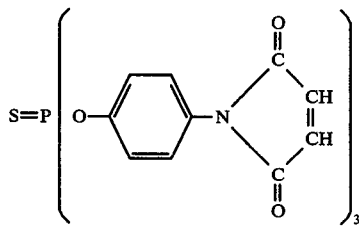

USE EXAMPLE I 69.3 g (0.13 mol) of the N,N′,N″-tris-maleimide of tris-(4-aminophenyl)-phosphate manufactured according to Example 1 (hereafter referred to as "tris-imide I") and 31.9 g (0.085 mol) of N,N′-bis-(benzylidene)-diaminodiphenylmethane are well mixed and the mixture is fused in an oil bath at 185° C and degassed in vacuo. The melt is poured into a mould of dimensions 150×150×4 mm and is subsequently cured for 2 hours at 160° C, 2 hours at 180° C and 2 hours at 200° C. The test data of the resulting sheet are shown in Table I.

COMPARISON EXAMPLE A 92.0 g (0.257 mol) of N,N′,4,4′-diaminodiphenylmethane-bis-maleimide and 48.0 g (0.128 mol) of N,N′-bis-(benzylidene)-4,4′-diaminodiphenylmethane are well mixed and the mixture is fused in an oil bath at 160° C and degassed in vacuo. The melt is cured under the conditions indicated in Use Example I, to give a moulding. The test data are listed in Table I.

Table 1

| Moulding according to | Flexural strength according to VSM* 77,103 (kg/mm$^2$) | Impact strength according to VSM 77,105 (kg.cm/cm$^2$) | Heat distortion point according to ISO/R**75 (° C) |
|---|---|---|---|
| Use example I | 7.5 | 3.1 | 242 |
| Comparison example A | 4.9 | 2.2 | 239 |

*VSM = Standard specifications of the Verein Schweizerischer Maschinenindustrieller
**ISO/R = Standard specifications of the International Standards Organisation/Recommendation

COMPARISON EXAMPLE B

In accordance with French Patent Specification No. 1,555,564, 19.8 g (0.10 mol) of 4,4'-diaminodiphenylmethane and 72.0 g (0.20 mol) of N,N'-4,4'-diaminodiphenylmethane-bis-maleimide are well mixed and the mixture is fused at 150° C and degassed. The melt is poured into a mould of dimensions 150×150×4 mm and is subsequently cured for 1.5 hours at 140° C, 1.5 hours at 160° C, 1.5 hours at 180° C and 1.5 hours at 200° C. The resulting moulding has a heat distortion point of 209° C according to ISO/R 75.

USE EXAMPLE II 7.28 g (0.0119 mol) of "tris-imide I" and 2.72 g (0.0169 mol) of benzylidene-n-butylamine are well mixed. The mixture is halved and one half is cured at 135° C and the other at 160° C.

USE EXAMPLE III 8.42 g (0.0137 mol) of "tris-imide I" and 1.58 g (0.0098 mol) of benzylidene-n-butylamine are well mixed. The mixture is halved and one half is cured at 135° C and the other at 160° C.

USE EXAMPLE IV 7.76 g (0.0127 mol) of "tris-imide I" and 2.64 g (0.0091 mol) of N,N'-bis-(benzylidene)-hexamethylenediamine are well mixed and cured at 160° C.

USE EXAMPLE V 8.48 g (0.00139 mol) of "tris-imide I" and 1.52 g (0.0052 mol) of N,N'-bis-(benzylidene)-hexamethylenediamine are well mixed and cured at 160° C.

COMPARISON EXAMPLE C

Attempts are made to gel or cure 5 g of "tris-imide I" at 135° C or 160° C in a test tube.

The gelling and curing times of Use Examples II – V and of Comparison Example C are listed in Table 2. The times are calculated from immersion of the sample into the heating bath to gelling or curing. Table 2 shows the very much shorter gelling and curing times of Use Examples II – V as compared to Comparison Example C, in which only the tris-imide I was used. However, it also shows the surprising fact that Use Examples III and V, in which more than 2 imide groups are present per >C=N— group in the reaction mixture, cure even more rapidly than Use Examples II and IV (at 160° C), in which the ratio of imide to >C=N— group corresponds to the cited publication.

Table 2

| Examples | Ratio of imide group to C=N group | | Condition of the mixture after the reaction time, indicated in minutes, at | | |
|---|---|---|---|---|---|
| | | | 135° C | | 160° C |
| | | | gelled | hard | gelled | hard |
| Use Example II | 2 | 1 | 19 | 43 | 9 | 14 |
| Use Example III | 4 | 1 | 16 | 41 | 8 | 14 |
| Use Example IV | 2 | 1 | — | — | 7 | 9 |
| Use Example V | 4 | 1 | — | — | 6 | 9 |
| Comparison Example C | — | | Not fused | | 38* | >38* |

*The melting point of the tris-imide is 173.5 – 177° C; the gelling time therefore had to be determined at 180° C bath temperature.

USE EXAMPLE VI 72.6 g (0.119 mol) of tris-imide I and 37.4 g (0.089 mol) of N,N'-bis-(benzylidene)-1,3-di-(γ-aminopropyl)-5,5-dimethyl-hydantoin are well mixed and the mixture is fused at 160° C in a round flask, and degassed. The clear melt is cast and cured as in Use Example I. The resulting moulding has the following properties:

| | |
|---|---|
| Flexural strength (according to VSm 77,103) | 9.6 kg/mm$^2$ |
| Impact strength (according to VSM 77,105) | 8.3 kg cm/cm$^2$ |
| Heat distortion point (according to ISO/R 75) | 241° C |

USE EXAMPLE VII 81.2 g (0.132 mol) of the tris-imide I and 31.2 g (0.10 mol) of N,N'-bis-(benzylidene)-p-xylylenediamine are well mixed and the mixture is fused at 150° C in a round flask, and degassed. The clear melt is cast and cured as in Use Example I. The resulting moulding shows the following properties:

| | |
|---|---|
| Flexural strength (VSM 77,103) | 10.1 kg/mm$^2$ |
| Impact strength (VSM 77,105) | 6.0 kg cm/cm$^2$ |
| Heat distortion point (ISO/R 75) | 267° C |

USE EXAMPLE VIII 80.8 g (0.132 mol) of the tris-imide I and 29.2 g (0.10 mol) of N,N'-bis-(benzylidene)-hexamethylenediamine are dissolved in 30 ml of hot dioxane. The solvent is stripped off again in vacuo at 150° C until a clear, bubble-free melt has been produced. This is cast and cured as in Use Example I. The moulding thus obtained shows the following properties:

| | |
|---|---|
| Flexural strength (VSM 77,103) | 10.1 kg/mm$^2$ |
| Impact strength (VSM 77,105) | 6.7 kg cm/cm$^2$ |
| Heat distortion point (ISO/R 75) | 245° C |

USE EXAMPLE IX 81.5 g (0.133 mol) of the tris-imide I and 28.4 g (0.10 mol) of N,N'-bis-(benzylidene)-p-phenylenediamine are mixed, fused and degassed as in Use Example VIII. The clear melt is cast and cured as in Use Example I. The test specimen thus obtained shows the following properties:

| | |
|---|---|
| Flexural strength (VSM 77,103) | 9.8 kg/mm² |
| Impact strength (VSM 77,105) | 7.4 kg cm/cm² |
| Heat distortion point (ISO/R 75) | 247° C |

USE EXAMPLE X 6.9 g of the N,N',N''-tris-maleimide of tris-(4-aminophenyl)-thiophosphate (manufactured according to Example 2) (hereafter referred to as "tris-imide II") and 3.1 g of N,N'-bis-(benzylidene)-4,4'-diaminodiphenylmethane are well mixed and cured in a rectangular frame of 1 mm thick polytetrafluoroethylene ("Teflon") between two 1 mm thick Teflon layers in a press at 180° C and under light pressure, not exceeding 5 atmospheres, for 15 minutes, to give a 1 mm thick moulding which is additionally post-cured at 200° C for 24 hours and of which the properties are shown in Table 3 and 4.

USE EXAMPLE XI 7.45 g of tris-imide II and 2.55 g of N,N'-bis-(benzylidene)-m-phenylenediamine are cured as in Example X to give a moulding of which the properties are indicated in Table 3 and 4.

USE EXAMPLE XII 6.6 g of tris-imide II and 3.4 g of N,N'-bis-(benzylidene)-4,4'-diaminodiphenyl-sulphone are cured as in Example X to give a moulding of which the properties are indicated in Table 3 and 4.

USE EXAMPLE XIII 7.75 g of tris-imide I and 2.25 g of N,N'-bis-(benzylidene)-ethylenediamine are cured as in Example X to give a moulding of which the properties are indicated in Table 3 and 4.

USE EXAMPLE XIV 6.50 g of tris-imide I and 3.50 g of N,N'-bis-(benzylidene)-4,4'-diaminodiphenyl-sulphone are cured as in Example X to give a moulding of which the properties are indicated in Table 3 and 4.

USE EXAMPLE XV 6.50 g of tris-imide I and 3.50 g of N,N'-bis-(benzylidene)-4,4'-diamino-3,3'-dichloro-diphenylmethane are cured as in Example X to give a moulding of which the properties are indicated in Table 3 and 4.

USE EXAMPLE XVI

A mixture is prepared as in Example XV, but 0.1 g of tert.-butyl perbenzoate is added additionally. The mixture is cured as in Example X to give a moulding of which the properties are indicated in Table 3 and 4.

USE EXAMPLE XVII 8.12 g of tris-imide I and 3.76 g of N,N'-bis-(benzylidene)-4,4'-diaminodiphenyl-ether were cured as in Example X to give a moulding of which the properties are indicated in Table 4.

USE EXAMPLE XVIII 8.12 g of tris-imide I and 2.84 g of terephthaldianil were cured as in Example X to give a moulding of which the properties are indicated in Table 4.

USE EXAMPLE XIX 8.12 g of tris-imide I and 3.54 g of N,N'-bis-(furylidene)-4,4'-diaminodiphenylmethane were cured as in Example X to give a moulding of which the properties are indicated in Table 4.

USE EXAMPLE XX 8.12 g of tris-imide I and 2.76 g of N,N'-bis-(cyclohexylidene)-hexamethylenediamine were cured as in Example X to give a moulding of which the properties are indicated in Table 4.

USE EXAMPLE XXI 6.11 g of tris-imide I and 1.90 g of isopropylidene-n-butylamine were cured as in Example X to give a moulding of which the properties are indicated in Table 4.

USE EXAMPLE XXII 8.12 g of tris-imide I and 2.44 g of terephthalylidene-di-(n-butyl-amine) were cured as in Example X to give a moulding of which the properties are indicated in Table 4.

The mouldings prepared in Examples X – XXII were subjected to a thermo-mechanical and thermo-gravimetric test. The thermo-mechanical test was carried out on the "T MS-1" instrument of Messrs. Perkin-Elmer at a speed of heating of 10° C/minute. The thermo-gravimetric analysis was carried out in dry air using the "Recording Vacuum Thermoanalyzer TA-1" instrument of Messrs. Mettler, with a sample of 50 mg and a speed of heating of 2° C/minute. In the thermo-gravimetric analysis, a curve of the weight of the sample as a function of the temperature is recorded ("thermo-gravimetric curve") and at the same time the first derivative of this thermo-gravimetric curve ("differentiated thermo-gravimetric curve") is drawn. The temperature of maximum speed of evaporation is the point of maximum slope of the thermo-gravimetric curve; at this temperature, the differentiated thermo-gravimetric curve shows a maximum. The proportion by weight which corresponds to the zone between two minima of the differentiated thermo-gravimetric curve is described as a fraction. The results of measurements by these methods of investigation are listed in Tables 3 and 4.

Table 3:

| Thermo-mechanical analysis | |
|---|---|
| Moulding according to | Start of softening (° C) |
| Use Example X | 250 |
| " XI | 331 |
| " XII | 278 |
| " XIII | 273 |
| " XIV | 301 |
| " XV | 334 |
| " XVI | 343 |

Table 3 shows the unusually high softening points, some of which are above 300° C, of the mouldings prepared according to the invention.

Table 4:

| | | Thermogravimetric analysis | | | | | | | | | |
|---|---|---|---|---|---|---|---|---|---|---|---|
| | | Maximum speed of decomposition (° C) fraction | | | | | Proportion of the fractions (%) | | | | | Weight loss, 1% ° per minute, at ° C |
| | | 1 | 2 | 3 | 4 | 5 | 1 | 2 | 3 | 4 | 5 | |
| Use Example | X | 100 | 360 | — | 570 | 750 | 1.3 | 8.6 | — | 48.9 | 41.2 | 340 |
| " | XI | 100 | 364 | — | 574 | 740 | 1.7 | 13.2 | — | 37.5 | 47.6 | 333 |
| " | XII | 120 | 344 | 492 | — | 712 | 1.4 | 14.4 | 48.2 | — | 36.0 | 320 |
| " | XIII | 100 | 320 | 467 | 745 | 884 | 2.3 | 10.8 | 38.1 | 41.3 | 7.6 | 290 |
| " | XIV | 110 | 332 | 515 | 710 | — | 2.0 | 12.3 | 50.6 | 35.1 | — | 312 |
| " | XV | 90 | 365 | 447 | 720 | — | 1.0 | 22.7 | 41.9 | 34.4 | — | 330 |
| " | XVI | 80 | 358 | 495 | 728 | — | 1.6 | 10.2 | 48.2 | 40.0 | — | 322 |
| " | XVII | 110 | 350 | 442 | 625 | 750 | 0.6 | 9.6 | 13.8 | 18.3 | 57.7 | 315 |
| " | XVIII | 90 | 356 | 500 | — | 745 | 1.2 | 6.4 | 45.2 | — | 47.2 | 345 |
| " | XIX | 75 | 361 | 442 | 560 | 752 | 2.5 | 8.9 | 10.2 | 27.2 | 51.2 | 345 |
| " | XX | 140 | 326 | 420 | 557 | 738 | 2.2 | 13.5 | 14.9 | 20.9 | 48.5 | 304 |
| " | XXI | 120 | 315 | 445 | — | 736 | 0.9 | 17.0 | 30.0 | — | 52.1 | 282 |
| " | XXII | 110 | 360 | 546 | 648 | 729 | 1.8 | 11.4 | 43.1 | 21.9 | 21.0 | 333 |

Table 4 shows that the mouldings, with the exception of Example XIII and XXI, only start to decompose above 300° C even if there is access of air, with the fractions of which the maximum speed of decomposition lies between 320° C and 360° C representing a proportion of weight of less than 25%.

We claim:
1. A bis-imide or tris-imide selected from the group consisting of the N,N'-bis-maleimide of 4,4'-diaminotriphenyl phosphate, the N,N'-bis-citraconimide of 4"-tertbutyl-4,4'-diaminotriphenyl phosphate, the N,N'-bis-maleimide of 3,3'-diamino-3"-dimethylaminotriphenyl phosphate, the N,N'-bis-itaconimide of bis-(4-aminophenyl)-bisphenylyl phosphate, the N,N'-bis-maleimide of bis-(4-aminophenyl)-2-naphthyl phosphate, the N,N',N"-tris-maleimide of tris(4-aminophenyl) phosphate, the N,N',N"-tris-citraconimide of tris-(4-aminophenyl)phosphate, the N,N'-bis-maleimide of 4,4'-diaminotriphenyl phosphite, the N,N'-bis-maleimide of diaminotriphenyl thiophosphate, the N,N',N"-tris-maleimide of tris-(4-aminophenyl) phosphite, the N,N',N"-tris-maleimide of tris-(4-aminophenyl) thiophosphate and the N,N',N"-trismaleimide of tris-(4-aminophenyl) thiophosphate.

2. Tris-maleimide according to claim 1 of the formula

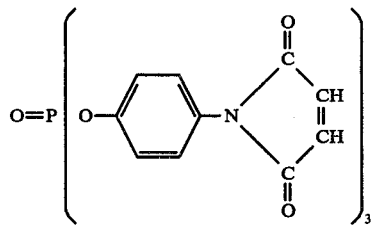

3. Tris-maleimide according to claim 1 of the formula

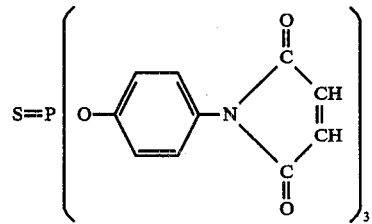

* * * * *